United States Patent
Morgan et al.

(10) Patent No.: US 7,556,638 B2
(45) Date of Patent: *Jul. 7, 2009

(54) RETROGRADE FIXATION TECHNIQUE WITH INSERT-MOLDED INTERFERENCE SCREW

(75) Inventors: Craig D. Morgan, Greenville, DE (US); Jeffrey Wyman, Naples, FL (US); Reinhold Schmieding, Naples, FL (US); Philip S. O'Quinn, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1188 days.

This patent is subject to a terminal disclaimer.

(21) Appl. No.: 10/358,192

(22) Filed: Feb. 5, 2003

(65) Prior Publication Data

US 2003/0120278 A1 Jun. 26, 2003

Related U.S. Application Data

(63) Continuation-in-part of application No. 10/256,076, filed on Sep. 27, 2002, now Pat. No. 7,063,171, which is a continuation-in-part of application No. 09/864,258, filed on May 25, 2001, now Pat. No. 6,461,373.

(60) Provisional application No. 60/207,235, filed on May 26, 2000.

(51) Int. Cl.
*A61B 17/04* (2006.01)

(52) U.S. Cl. .............. 606/232; 606/321; 623/13.14

(58) Field of Classification Search ............... 606/53, 606/73, 148, 228–233, 104, 300, 304, 310, 606/321, 331, 908; 623/13.14
See application file for complete search history.

(56) References Cited

U.S. PATENT DOCUMENTS

| | | | | | |
|---|---|---|---|---|---|
| 4,870,957 | A | * | 10/1989 | Goble et al. | 623/13.12 |
| 4,946,462 | A | * | 8/1990 | Watanabe | 606/148 |
| 4,950,270 | A | * | 8/1990 | Bowman et al. | 606/916 |
| 5,156,616 | A | * | 10/1992 | Meadows et al. | 606/232 |
| 5,456,685 | A | * | 10/1995 | Huebner | 606/321 |
| 5,549,617 | A | * | 8/1996 | Green et al. | 606/144 |
| 5,571,139 | A | * | 11/1996 | Jenkins, Jr. | 606/232 |
| 5,603,716 | A | | 2/1997 | Morgan et al. | |
| 5,632,748 | A | * | 5/1997 | Beck et al. | 606/89 |
| 5,643,320 | A | | 7/1997 | Lower et al. | |
| 5,658,289 | A | * | 8/1997 | Boucher et al. | 623/13.14 |
| 5,662,658 | A | * | 9/1997 | Wenstrom, Jr. | 606/104 |
| 5,674,224 | A | * | 10/1997 | Howell et al. | 606/88 |
| 5,681,333 | A | * | 10/1997 | Burkhart et al. | 606/148 |

(Continued)

*Primary Examiner*—Eduardo C Robert
*Assistant Examiner*—James L Swiger
(74) *Attorney, Agent, or Firm*—Dickstein Shapiro LLP

(57) ABSTRACT

Endosteal fixation of a ligament graft with a bioabsorbable interference screw installed in a retrograde manner in ACL reconstruction. The bioabsorbable interference screw is insert-molded with a length of suture extending from the distal tip of the screw for pulling the interference screw into the joint and into position for retrograde insertion at the top of the tibial tunnel. The interference screw has a cannulation extending partially through the screw from the leading tip. The cannulation is shaped to receive a correspondingly shaped driver. The driver is inserted into the tibial tunnel to engage the screw. By turning the driver, the interference screw is turned into the tibial tunnel in a retrograde manner. Accordingly, interference fixation of the graft near the tibial plateau is provided, thereby eliminating graft abrasion at the tibial plateau tunnel opening.

1 Claim, 3 Drawing Sheets

U.S. PATENT DOCUMENTS

| | | | |
|---|---|---|---|
| 5,720,766 A | 2/1998 | Zange et al. | |
| 5,733,307 A | 3/1998 | Dinsdale | |
| 5,860,978 A * | 1/1999 | McDevitt et al. | 606/72 |
| 5,871,504 A | 2/1999 | Eaton et al. | |
| 5,891,146 A * | 4/1999 | Simon et al. | 606/71 |
| 5,964,783 A * | 10/1999 | Grafton et al. | 606/232 |
| 6,036,694 A * | 3/2000 | Goble et al. | 606/72 |
| 6,146,387 A * | 11/2000 | Trott et al. | 606/104 |
| 6,152,934 A * | 11/2000 | Harper et al. | 606/139 |
| 6,273,890 B1 | 8/2001 | Frazier | |
| 6,319,270 B1 | 11/2001 | Grafton et al. | |
| 6,355,053 B1 | 3/2002 | Li | |
| 6,355,066 B1 | 3/2002 | Kim | |
| 6,461,373 B2 * | 10/2002 | Wyman et al. | 606/232 |
| 6,527,794 B1 * | 3/2003 | McDevitt et al. | 606/232 |
| 6,629,977 B1 * | 10/2003 | Wolf | 606/73 |
| 6,746,483 B1 * | 6/2004 | Bojarski et al. | 623/13.14 |
| 2003/0004545 A1 | 1/2003 | Burkhart et al. | |
| 2004/0106950 A1 * | 6/2004 | Grafton et al. | 606/232 |

* cited by examiner

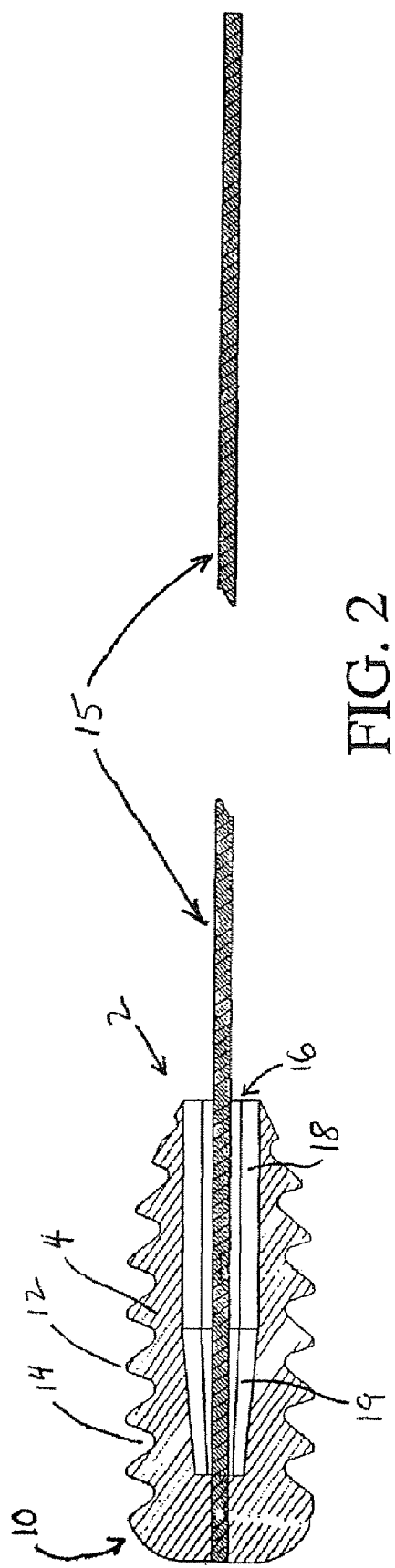
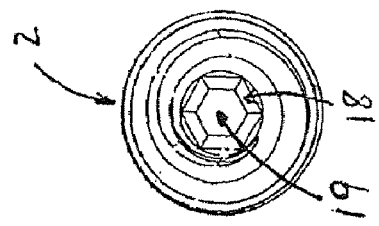
FIG. 2
FIG. 3

RETROGRADE FIXATION TECHNIQUE WITH INSERT-MOLDED INTERFERENCE SCREW

This is a continuation-in-part of U.S. application Ser. No. 10/256,076, filed Sep. 27, 2002, now U.S. Pat. No. 7,063,717, which is a continuation-in-part of U.S. application Ser. No. 09/864,258, filed May 25, 2001, now U.S. Pat. No. 6,461,373, and claims the benefit of U.S. Provisional Application Ser. No. 60/207,235, filed May 26, 2000.

FIELD OF THE INVENTION

The present invention relates to interference screw fixation of replacement ligament grafts, and more particularly to methods and apparatus for retrograde placement and installation of an interference screw for graft fixation in a bone tunnel.

BACKGROUND OF THE INVENTION

Methods of anterior cruciate ligament (ACL) reconstruction using interference screw fixation are described in U.S. Pat. Nos. 5,211,647 and 5,320,626, the entire disclosures of which are incorporated herein by reference. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels requires a drill guide, such as those disclosed in U.S. Pat. Nos. 5,269,786 and 5,350,383, which also are incorporated herein by reference.

One drawback of the described tenodesis methods is that the ligament graft is secured only at the bottom of the tibial tunnel. The graft is not secured at the top end of the tibial tunnel. Consequently, the graft is free to move from side to side, resulting in a "windshield wiper" effect, during which the graft abrades against the upper rim of the tibial tunnel, shortening the life of the ACL repair.

U.S. Pat. No. 5,603,716 to Morgan et al. discloses a technique for ACL reconstruction that avoids the above-noted problem of graft abrasion. The method disclosed by Morgan et al. requires forming two closed-ended sockets, one in the tibia and the other in the femur. However, forming a femoral socket is difficult without a tibial tunnel for insertion of a femoral guide and drill.

Accordingly, the need exists for a method of ACL reconstruction that provides anatomical graft fixation at the tibial plateau, and without the need for forming two separate bone sockets.

SUMMARY OF THE INVENTION

The present invention overcomes the disadvantages of the prior art, such as those noted above, by providing methods and apparatus for endosteal fixation of a ligament graft using an interference screw that is installed in a retrograde manner. In a preferred embodiment, anterior cruciate ligament (ACL) reconstruction is performed using an interference screw installed in a retrograde manner through the tibial plateau to secure an ACL graft at the top of the tibial tunnel.

The interference screw is insert-molded with a length of suture. The suture extends beyond the leading tip of the screw a sufficient length to allow the suture to be passed through the tibial tunnel and to be grasped for pulling the screw into the tibial tunnel through the top tibial plateau opening. The screw and suture preferably are bioabsorbable.

A driver for the screw fits into a cannulation in the leading end of the screw. Preferably, the driver is cannulated to accept the length of suture extending from the bottom opening of the tibial tunnel, and has means for grasping the suture to assist the surgeon in pulling the interference screw into the top opening of the tibial tunnel. The screw is blind headed (not filly cannulated) to eliminate synovial fluid leak through the screw into the tibial tunnel.

According to a preferred method of the present invention, the suture extending from the interference screw is fed through the joint cavity into the top tibial plateau opening of the tunnel, and down through the tibial tunnel to exit at the anterior surface of the tibia. The free end of suture exiting the anterior surface of the tibial tunnel preferably is inserted through the cannulation of the cannulated driver and secured around a post on the driver.

After the ligament graft has been placed in the tibial tunnel, the suture is drawn using the driver at the anterior opening of the tibial tunnel to pull the interference screw into the joint cavity in a retrograde fashion. The knee joint is positioned to allow the end of the screw to be manipulated into the top opening of the tibial tunnel, with the screw being pivoted within the joint cavity to align axially with the tunnel and the driver.

With the screw being drawn into a position of alignment with the tunnel, the driver is advanced into the tibial tunnel. Pulling on the suture retains the screw in position for engagement with the driver by applying tension to the suture in the direction opposing driver insertion.

Once the driver has engaged the screw, turning the driver causes the screw to advance, or "back in" to the tunnel in retrograde fashion. Using a right-threaded screw, a surgeon will turn the screw counter-clockwise. In an alternative embodiment, the screw has reverse threads, so that turning the driver clockwise advances the screw into the tunnel. The screw is turned into the tunnel until the back end of the screw is substantially flush with the tibial plateau, and has been installed to a depth sufficient to provide interference fixation of the graft at the top of the tunnel. The driver is disengaged from the screw, and excess suture is removed.

The insert-molded interference screw of the present invention can also be inserted forwardly into the femur to fixate a ligament graft in the femoral socket by passing the suture extending from the leading tip of the screw through a narrow tunnel drilled through the femur in alignment with the femoral socket, and drawing on the suture to pull the screw into the femoral socket.

Other features and advantages of the present invention will become apparent from the following description of the invention which refers to the accompanying drawings.

BRIEF DESCRIPTION OF THE DRAWINGS

FIG. 2 is a cross-sectional elevation of the screw and inserted-molded suture of FIG. 1.

FIG. 3 is a proximal end view of the screw of FIGS. 1 and 2.

FIG. 4 is an elevation of a driver for the screw of FIGS. 1-3 according to the present invention.

FIG. 5 is a cross-sectional plan view of the driver of FIG. 4.

DETAILED DESCRIPTION OF THE PREFERRED EMBODIMENTS

Figure 1:
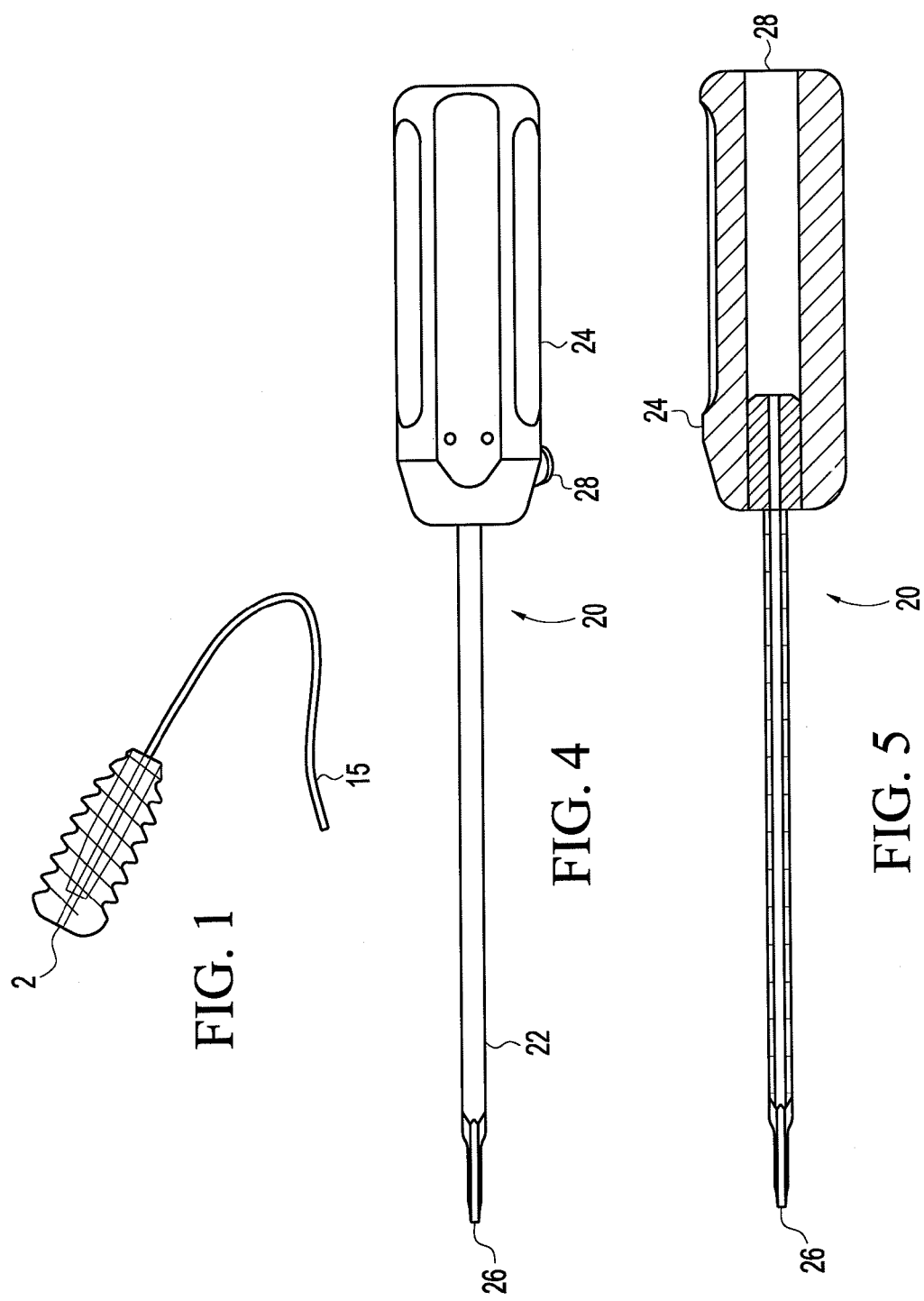
FIG. 1 is a perspective view of an interference screw with insert-molded suture according to the present invention.

Referring initially to FIGS. 1-3, a bioabsorbable interference screw 2 for tenodesis of an anterior cruciate ligament graft is shown. Body 4 of the screw 2 features a continuous thread 6 provided substantially along the length of the body from a blunt front end 8 to a rounded back end 10. The thread preferably has flattened crests 12 and flattened troughs 14 to obviate ligament graft damage by the screw threads and enhance graft fixation. A length of suture 15 is insert-molded into interference screw 2 in a manner similar to that described in U.S. Pat. No. 5,964,783 and U.S. Patent Application Publ. No. 2003/0004545 A1, the disclosures of which are herein incorporated by reference. The suture may be a conventional surgical suture or an ultrastrong surgical suture, e.g., Fiber Wire suture, sold by Arthrex, Inc. of Naples, Fla., the assignee of the present application. Fiber Wire suture is formed of ultrahigh molecular weight polyethylene and is described in U.S. Ser. No. 09/950,598, the disclosure of which is herein incorporated by reference.

The cannulated body 4 of bioabsorbable interference screw 2 tapers toward the front end 8 to terminate in a blunt tip 16. The taper eases entry of the screw into the tibial tunnel according to the preferred method of ligament graft fixation described further below. The blunt tip 16 of the screw prevents damage of the ligment graft during insertion of the screw. The rounded back end 10 of the screw minimizes abrasion and wear of the installed ligament graft. Cannula 18, 19 formed through screw body 4 has a hexagonal shape for engaging a correspondingly shaped driver as described below. Preferably, distal portion 18 of the screw cannula is straight, and proximal portion 19 of the screw cannula is tapered. To reduce loss of synovial fluid leak through the screw into the tunnel, the cannula does not extend completely to the back end screw, but rather terminates internally as shown. The hexagonal shape of cannula 18, 19 is shown clearly in FIG. 3. The preferred screw is 20 mm long, and is provided in diameters of 8 mm, 9 mm, and 10 mm.

Referring to FIGS. 4 and 5, a driver 20 for installing the interference screw of the present invention is shown. Driver 20 includes a cannulated shaft 22 attached to a cannulated handle 24. A drive tip 26 formed at the distal end of shaft 22 has a straight/tapered, hexagonal shape conforming to straight/tapered cannula 18, 19 of screw 2. At the proximal end of the handle, a post 28 is provided for securing suture.

Figure 6:
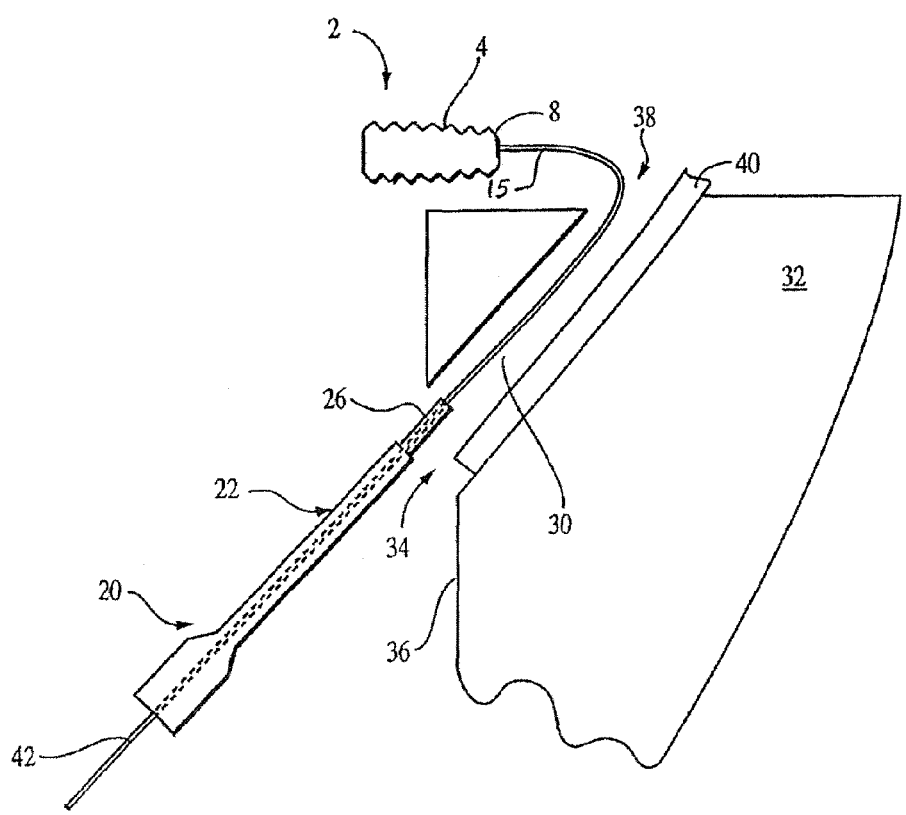
FIG. 6 schematically illustrates fixation of an ACL graft using the retrograde biointerference screw of the present invention, and in accordance with one embodiment of the invention.

A method of ACL tenodesis according to a preferred embodiment of the present invention includes forming a tunnel 30 in a tibia 32, as shown in FIG. 6. The tunnel is formed with a diameter appropriate for interference fixation based on the size of the selected screw 2. Tunnel 30 ascends at an angle posteriorly from a bottom opening 34 at an anterior tibial surface 36 toward an upper opening 38 at the tibial plateau. The lower end of an ACL graft 40 is inserted into the tunnel through the tibial plateau.

Screw 2 is inserted into the joint and through the tunnel 30 so that the free end of the insert-molded suture 15 exits the bottom opening 34. Suture passing instruments known in the art can be utilized.

The free end of the suture is used to draw screw 2 toward the tibial opening 38, either by hand or using driver 20 by threading the suture through the driver 20 and securing the suture onto post 28, for example. With the knee joint distended, the screw 2 is manipulated into the tibial plateau opening 38 and pivoted into axial alignment with the tunnel 30. Driver 20 is advanced into the tunnel 30 to achieve engagement with screw 2. Once the driver and screw are engaged, rotation of the screw with the driver advances the screw into the tunnel 30 in a retrograde manner. Screw insertion is continued until the back end 10 of screw 2 is substantially flush with the tibial plateau and the graft 40 is secured sufficiently within the tunnel. The driver 20 and any excess suture 15 is removed from the tunnel to complete this portion of the procedure.

The insert-molded interference screw of the present invention can also be inserted into the femur to fixate a ligament graft in the femoral socket by passing the suture extending from the leading tip of the screw through a narrow tunnel drilled through the femur in alignment with the femoral socket, and drawing on the suture to pull the screw into the femoral socket. The screw can then be turned into the socket forwardly with a screwdriver inserted through the tibial tunnel (the screw in this case having a back end cannulation) or in retrograde fashion with a screwdriver inserted through the narrow femoral tunnel (the screw in this case having a leading end cannulation).

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of anterior cruciate ligament reconstruction, comprising the steps of:

forming a tibial tunnel between an anterior tibial surface and the tibial plateau, the tibial plateau being adjacent a joint cavity;

positioning a ligament graft in the tibial tunnel;

subsequently passing a length of a suture extending from a distal end of an interference screw into the joint cavity and down through the tibial tunnel by way of an opening in the tibial plateau, the suture being insert-molded into the interference screw, the interference screw being partially cannulated at its distal end; and drawing on a free end of the suture exiting the anterior surface of the tibial tunnel to pull the interference screw, distal end first, into the joint cavity in a retrograde fashion;

inserting the free end of the suture into a cannulation of a cannulated screwdriver; and engaging the screwdriver with the cannulation at the distal end of the interference screw, and rotating the screwdriver to turn the interference screw into the tibial tunnel.

* * * * *